United States Patent [19]

Nishizawa et al.

[11] Patent Number: 4,814,059

[45] Date of Patent: Mar. 21, 1989

[54] ELECTROCHEMICAL DEVICE HAVING A HEATER AND LEAK PROTECTION ELECTRODE

[75] Inventors: Hitoshi Nishizawa, Iwakura; Kazuyoshi Shibata, Nagoya, both of Japan

[73] Assignee: NGK Insulators, Ltd., Nagoya, Japan

[21] Appl. No.: 162,489

[22] Filed: Mar. 1, 1988

[30] Foreign Application Priority Data

Mar. 3, 1987 [JP] Japan ................... 62-48245

[51] Int. Cl.$^4$ .......................................... G01N 27/58
[52] U.S. Cl. ................................. 204/406; 204/410; 204/412
[58] Field of Search ............ 204/410, 412, 425, 426, 204/1 S, 406

[56] References Cited

U.S. PATENT DOCUMENTS 4,400,260 8/1983 Stahl et al. ...................... 204/426

FOREIGN PATENT DOCUMENTS 59-197851 11/1984 Japan .

*Primary Examiner*—G. L. Kaplan
*Attorney, Agent, or Firm*—Parkhurst, Oliff & Berridge

[57] ABSTRACT

An electrochemical device including an electrochemical cell having a first solid electrolyte, and at least one pair of electrodes formed on the first soild electrolyte, and a heating portion having a second solid electrolyte, a first elctrically insulating ceramic layer formed on the second solid electrolyte, and a heater electrically insulated from the second solid electrolyte by the first insulating layer. The device further includes a second electrically insulating ceramic layer interposed between the first and second solid electrolytes, so as to electrically insulate these solid electrolytes from each other, and a protective electrode formed in contact with the second solid electrolyte of heating portion. The protective electrode is electrically connected to at least one of the of electrodes of the electrochemical cell.

7 Claims, 3 Drawing Sheets

ELECTROCHEMICAL DEVICE HAVING A HEATER AND LEAK PROTECTION ELECTRODE

BACKGROUND OF THE INVENTION

1. Field of the Invention

The present invention relates in general to an electrochemical device, and more particularly to an electrochemical device which has an integrally formed heating portion for heating an electrochemical cell.

2. Discussion of the Prior Art

A sensor which employs an oxygen-ion conductive solid electrolyte material such as zirconia ceramic is known as an oxygen sensor operable according to an oxygen concentration cell, for determining the concentration of oxygen contained in emissions produced by internal combustion engines for motor vehicles, or in industrial furnaces or boilers. Other electrochemical devices similar to such oxygen sensors, which utilize the principle of a concentration cell, are also known, as detectors for detecting hydrogen, nitrogen or carbon dioxide, or as pumps associated with these components.

The electrochemical device as indicated above includes an electrochemical cell which consists of a suitable solid electrolyte and at least one pair of electrodes formed in contact with the solid electrolyte, as well known in the art. For assuring an accurate and reliable operation of the cell of the electrochemical device even while the temperature of a gas to be measured is relatively low, various heating means or heat-generating members have been proposed to heat a detecting portion of the electrochemical cell, i.e., a portion at which the electrodes are disposed, so that the detecting portion is maintained at a suitable operating temperature. Such heating means or heat-generating members are provided as an integral part of an electrochemical element which has the electrochemical cell.

However, a current applied to such integrally built-in heating means to heat the electrochemical cell may leak toward the cell, and the output of the cell may be adversely influenced by the leak current. While the use of a suitable electrically insulating layer between the electrochemical cell and the heating means is proposed in the art, the insulating layer alone cannot be a satisfactory solution to the above problem.

In light of the above problem, an arrangement employing a protective or shielding electrode between the electrochemical cell and the heating means is disclosed in U.S. Pat. No. 4,400,260 (DE No. P3120159.8) and Japanese Patent Application Laid-open Publication No. 59-197851 (published in 1984), for example. In the disclosed arrangement, the protective electrode is embedded in a portion of a solid electrolyte body of the electrochemical cell or formed in contact with the solid electrolyte body, and the heater or heating means is disposed on the solid electrolyte body via an electrically insulating layer. Alternatively, electrically insulating layers are provided on opposite sides of a measuring electrode which is adapted to also function as the protective electrode. In this case, the heater is disposed on one of the two insulating layers, while the solid electrolyte body of the electrochemical cell is diposed on the other insulating layer. In either case, the electrochemical element is adapted so that the leak current from the heater flows to the protective electrode.

However, the above-described known arrangement using the protective electrode has various potential problems that should be solved. For instance, where the protective electrode is disposed in contact with the solid electrolyte body of the electrochemical cell, there may be induced an electromotive force between the protective electrode and one of the electrodes of the electrochemical cell, based on a difference in the oxygen partial pressure between the atmospheres contacting these two electrodes, if the two electrodes are electrically connected to each other.

In the case where the protective electrode is embedded in the solid electrolyte body or covered by a layer having a high gas-diffusion resistance, ions flow from a portion of the solid electrolyte body surrounding the protective electrode, due to the leak current from the heater, whereby that solid electrolyte portion is deteriorated.

In the case where the electrochemical element includes two electrically insulating layers which are disposed on the opposite sides of the protective electrode and are interposed between the solid electrolyte body of the electrochemical cell and the heater, the surface area of the protective electrode should be large enough to shield the leak current from the heater. That is, if the heater has a size sufficiently large for heating the electrochemical element to a desired operating temperature, the protective electrode should be accordingly large-sized. In this case, the cost of manufacture of the electrochemical element whose laminar structure includes the electrochemical cell, heater, protective electrode and insulating layers is inevitably increased. Further, the strength and durability of the electrochemical element, which is substantially an integral ceramic mass, are reduced due to the presence of the protective electrode in the ceramic mass, which electrode is substantially a metal layer heterogeneous to the ceramic mass of the electrochemical element. A solution to these problems requires the use of a heater which has a relatively small surface area for heat generation, i.e., a relatively small heating capacity.

SUMMARY OF THE INVENTION

The present invention was made in light of the above problems encountered in the prior art. It is therefore a principal object of the present invention to provide an electrochemical device which has provisions for preventing or minimizing a flow of a leak current from a heater to an electrochemical cell, thereby effectively improving its detecting accuracy.

Another object of the invention is to provide an electrochemical device using a protective electrode for a heater, which protective electrode is neither embedded in a solid electrolyte body of an electrochemical cell while extending over the entire distance between the heater and the electrochemical cell, nor has an increased surface area corresponding to the heat generating surface area, whereby the protective electrode neither reduces the strength of the electrochemical element having the cell, nor increases the cost of fabrication of the device.

The above objects may be achieved according to the principle of the present invention, which provides an electrochemical device including an electrochemical element having an integrally formed laminar structure comprising: (a) at least one electrochemical cell including a first solid electrolyte, and at least one pair of electrodes formed in contact with the first solid electrolyte; (b) at least one heating portion including a second solid electrolyte, a first electrically insulating ceramic layer formed in contact with the second solid electrolyte, and a heater electrically insulated from the second solid electrolyte by the first electrically insulating ceramic layer; (c) a second electrically insulating ceramic layer interposed between the first solid electrolyte of the above-indicated at least one electrochemical cell and the second solid electrolyte of the above-indicated at least one heating portion, so as to electrically insulate the first and second solid electrolytes from each other; and (d) a protective electrode formed in contact with the second solid electrolyte of the above-indicated at least one heating portion. The protective electrode is electrically connected to at least one of the above-indicated at least one pair of electrodes of the above-indicated at least one electrochemical cell.

In the electrochemical device of the present invention constructed as described above, the first electrically insulating ceramic layer, the second solid electrolyte and the second electrically insulating ceramic layer are disposed between the heater of the heating portion and the electrochemical cell or cells, while the protective electrode is formed in contact with the second solid electrolyte. A leak current from the heater can be effectively shielded by the protective electrode, which is connected to at least one of the electrodes of the electrochemical cell or cells. Thus, an output error of each electrochemical cell due to the leak current can be reduced, and the detecting accuracy of the device is accordingly improved. Further, the instant device eliminates an otherwise necessary increase in the surface area of the protective electrode according to the heat generating surface area of the heater. Furthermore, in the instant arrangement wherein the protective electrode is not embedded in the laminar structure of the electrochemical cell or cells, the protective electrode will neither lower the strength of the electrchemical element nor increase its cost of manufacture. These are significant advantages provided by the present invention.

Preferably, the protective electrode is electrically connected to a negative voltage terminal of the heater of the heating portion, so that the potential of the second solid electrolyte is equal to that of the negative voltage terminal of the heater. In this form of the invention, the deterioration of the second solid electrolyte due to the leak current from the heater can be effectively avoided.

In another preferred form of the present invention, at least a portion of the protective electrode is substantially exposed to a predetermined gaseous fluid, so that the ions which flow from a portion of the second solid electrolyte adjacent to the protective electrode may be compensated for by the supply of ions from the gaseous fluid back into that portion of the second solid electrolyte, in order to prevent the deterioration of the portion of the second solid electrolyte which contacts the protective electrode.

In a further preferred form of the invention, the protective electrode and the electrode or electrodes of the electrochemical cell or cells are exposed to a substantially same gaseous fluid, in order to prevent an electromotive force from being induced between the protective electrode and the cell electrode due to a difference in the oxygen partial pressure between these electrodes, whereby an output error of the electrochemical cell or cells due to such undesirable electromotive force can be eliminated.

The second solid electrolyte may be a substantially gas-tight structure which surrounds at least a heat-generating portion of the heater, so that the heater is protected from the gas to be detected. This arrangement is capable of preventing otherwise possible diffusion or deterioration of the metal of the heater during operation of the electrochemical element at a relatively high temperature or in a reducing atmosphere. That is, the durability of the heater can be significantly improved.

The electrochemical element of the instant device may use only one electrochemical cell as a sensing cell or a pumping cell, or two electrochemical cells one of which is used as an electrochemical pumping cell and the other of which is used as an electrochemical sensing cell. In the latter case, the protective electrode may preferably be electrically connected to an inner pumping electrode of the pumping cell and a measuring electrode of the sensing cell, which pumping and measuring electrodes are exposed to substantially a same gaseous fluid. Alternatively, the protective electrode may be electrically connected to a reference electrode of the sensing cell.

BRIEF DESCRIPTION OF THE DRAWINGS

The above and optional objects, features and advantages of the present invention will become more apparent by reading the following detailed description of some presently preferred embodiments of the invention, when considered in conjunction with the accompanying drawings, in which.

DETAILED DESCRIPTION OF THE PREFERRED EMBODIMENTS

Figure 1:
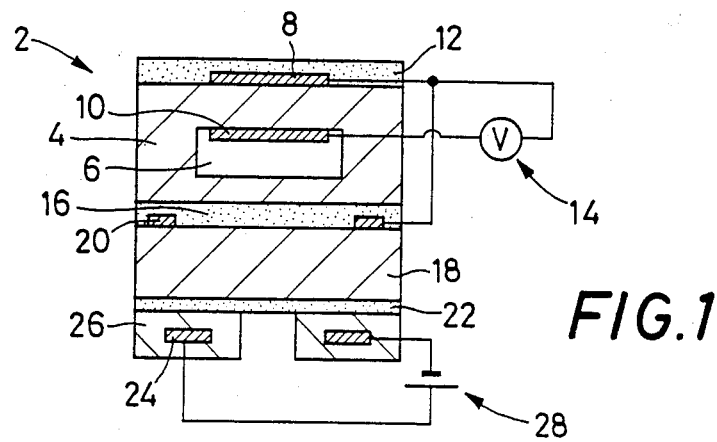
FIG. 1 through FIG. 4 are schematic elevational views in transverse cross section of a detecting portion of different embodiments of an electrochemical device in the form of an oxygen sensor according to the present invention, respectively, the detecting portion being located at one longitudinal end of each oxygen sensor.

Referring first to the transverse cross sectional view of FIG. 1, there is shown the detecting portion of an electrochemical element (oxygen sensing element) of an electrochemical device in the form of an oxygen sensor according to one embodiment of the present invention. The detecting portion is provided at one of opposite longitudinal ends of the electrochemical element. This electrochemical element, which is indicated at 2 in FIG. 1, is an integral, planar, elongate, laminar structure having a relatively small width, as well known in the art. The detecting portion at the above-indicated one longitudinal end of the electrochemical element is operated according to the principle of a concentration cell.

The electrochemical element 2 indicated above is formed by known laminating techniques. The element 2 includes a planar solid electrolyte body 4 made of a suitable solid electrolyte such as zirconia ceramic, which exhibits a high degree of oxygen-ion conductivity at an elevated temperature. The planar solid electrolyte body 4 has an air passage 6 formed therein so as to extend in the longitudinal direction. This air passage 6 communicates with the ambient air, at the other longitudinal end of the electrochemical element. On a major outer surface of the solid electrolyte body 4, there is formed a porous measuring electrode 8 made of a cermet consisting of platinum and zirconia, or other suitable material, such that the electrode 8 is held in close contact with the outer surface. A similar porous electrode 10 as a reference electrode is formed in contact with an inner surface of the solid electrolyte body 4, such that the reference electrode 10 communicates with the atmosphere which exists within the air passage 6 as a reference gas. The outer measuring electrode 8 is covered by a porous protective layer 12 made of alumina, for example, and is thus protected by this layer from direct exposure to an external gas to be measured by the instant electrochemical device (hereinafter referred to as "measurement gas"). In other words, the measuring electrode 8 is exposed to the measurement gas through the porous structure of the protective layer 12. In this arrangement, the solid electrolyte body 4, and the measuring and reference electrodes 8, 10 formed in contact with the solid electrolyte body 4, cooperate with each other to constitute an electrochemical cell which functions as a concentration cell. As is well known in the art, an electromotive force is induced between the measuring and reference electrodes 8, 10, according to a difference in oxygen partial pressure between the atmospheres with which the electrodes communicate. The induced electromotive force is detected by an external voltage measuring means 14.

On the side of the planar solid electrolyte body 4 remote from the measuring electrode 8, there is formed a porous inner electrically insulating layer 16 formed of alumina or similar material. On this inner insulating layer 16 is formed a solid electrolyte layer 18 which is made of a solid electrolyte material such as zirconia ceramic, as used for the solid electrolyte body 4. In the inner insulating layer 16, there is embedded a protective electrode 20, such that the electrode 20 is in contact with the surface of the solid electrolyte layer 18 which contacts the insulating layer 16. This protective electrode 20 is electrically connected to the measuring electrode 8 of the electrochemical cell described above.

The outer surface of the solid electrolyte body 18 is covered by a porous outer electrically insulating layer 22 made of alumina or similar material. On the outer insulating layer 22, there is formed a highly dense electrically insulating layer 26 which is made of highly electrically resistive zirconia or similar material. This highly dense insulating layer 26 has a heater 24 embedded therein as an integral part thereof. The heater 24 is connected to an external power source 28, so that the energized heater 24 heats at least the end portion of the electrochemical element 2 at which the detecting portion is provided, in order to maintain a suitable operating temperature of the detecting portion.

In summary, the electrochemical element 2 described above is constructed such that the first electrically insulating ceramic layer (22, 26) and the second electrically insulating ceramic layer (16) are disposed between the solid electrolyte body 4 of the electrochemical cell and the heater 24, while the solid electrolyte layer 18 is disposed between the first and second electrically insulating ceramic layers, such that the protective electrode 20 electrically connected to the measuring electrode 8 of the electrochemical cell is held in contact with the solid electrolyte layer 18.

In the thus constructed electrochemical element 2, a leak current from the heater 24 is effectively led to the protective electrode 20 through the electrically conductive solid electrolyte layer 18, but is prevented by the inner insulating layer 16 from flowing into the electrochemical cell. Therefore, the instant arrangement avoids an adverse effect of the leak current from the heater 24, on the electromotive force (i.e., output) induced in the electrochemical cell (4, 8, 10) based on an oxygen partial pressure difference between the measurement gas and the reference gas. Accordingly, the accuracy of detection of the measurement gas based on the output of the cell is effectively improved.

Further, since the protective electrode 20 is exposed to the measurement gas or atmosphere through the porous inner insulating layer 16 (second electrically insulating ceramic layer), the electrode 20 is supplied with oxygen ions from the measurement gas. Consequently, a portion of the solid electrolyte layer 18 which contacts the protective electrode 20 is not deteriorated by a flow of the leak current from the heater to the protective electrode 20 through the solid electrolyte layer 18. The second electrically insulating ceramic layer 16 provides a sufficient insulating effect even though its thickness is smaller than that of the first electrically insulating ceramic layer 22, 26, since the second ceramic layer 16 is not in direct contact with the heater 24 and is not locally heated.

Furthermore, the leak current from the heater 24 is effectively led to the protective electrode 20 through the solid electrolyte layer 18, since the electrode 20 is in contact with the layer 18. This arrangement does not require the protective electrode 20 to have an increased surface area, even if the surface area of the heater 24 is increased. Namely, the protective electrode 20 may function with a relatively small surface area contacting the solid electrolyte layer 18, and therefore does not cause inconveniences such as reduction in the strength and durability of the electrochemical element 2, or increase in the cost of manufacture.

Figure 2:
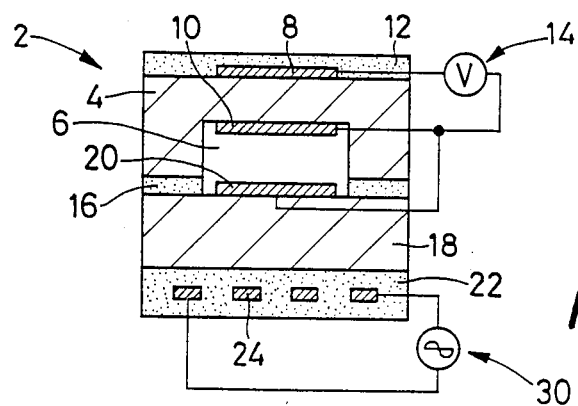

Referring next to FIG. 2, there is shown another form of the electrochemical element 2 which uses a concentration cell similar to that of the electrochemical element 2 shown in FIG. 1 However this electrochemical element 2 of FIG. 2 is different from the element of FIG. 1, in that the protective electrode 20 is disposed in contact with the solid electrolyte layer 18 such that the electrode 20 is exposed to the air passage 6 and electrically connected to the reference electrode 10 also exposed to the air passage 6. Another difference of the instant electrochemical element 2 from that of FIG. 1 lies in that the heater 24 is embedded in the outer insulating layer 22 and electrically connected to a power source in the form of an AC power source 30 (e.g., 10 KHz sine wave current). The other components of this electrochemical element 2 are identical with the corresponding components of the element 2 of FIG. 1. These corresponding components are identified by the same reference numerals in FIGS. 1 and 2, and redundant description of these components will not be provided.

In the electrochemical element 2 constructed as illustrated in FIG. 2, both the reference electrode 10 of the electrochemical cell and the protective electrode 20 are exposed to the air passage 6, that is, communicate with the same atmosphere, i.e., ambient air as the reference gas. Consequently, there is induced no electromotive force between the two electrodes 10 and 20, due to a difference in the oxygen partial pressure. This results in improvement in the detecting accuracy of the electrochemical element 2. In addition, the inner electrically insulating layer 16 prevents the leak current from the heater 24 from flowing into the electrochemical cell (4, 8, 10), while the solid electrolyte layer 18 permits the leak current to be effectively led to the protective electrode 20, whereby an error in the output of the electrochemical element 2 due to the leak current is suitably reduced or eliminated.

Moreover, the instant electrochemical element 2 does not include a metal layer between the solid electrolyte body 4 of the electrochemical cell and the heater 24, since the protective electrode 20 as a metal layer is disposed within the air passage 6. In this sense, the electrochemical cell and the ceramic layer (inner insulating layer 16, solid electrolyte layer 18 and outer insulating layer 22) can be well integrated as a unitary laminar structure having an increased strength.

Figure 3:
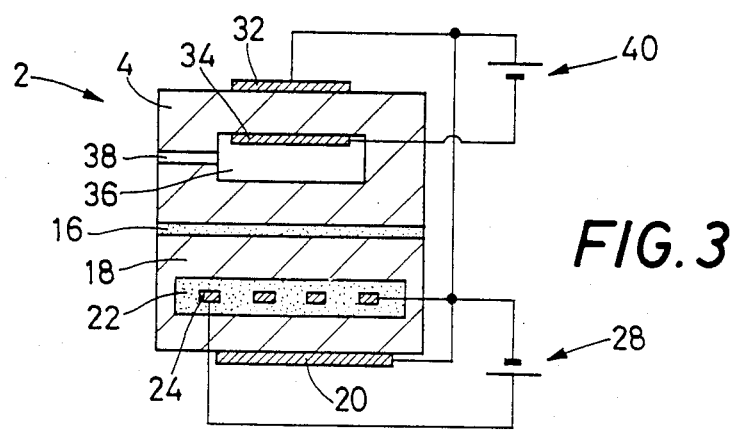

Reference is now made to FIG. 3 wherein the electrochemical element 2 has an electrochemical cell in the form of an electrochemical pumping cell which includes the solid electrolyte body 4, and an outer and an inner pumping electrode 32, 34 formed in contact with the solid electrolyte body 4. In this pumping cell, the measurement gas in the external space is introduced into an internal space 36 to which the inner pumping electrode 34 is exposed, through a pin hole 38 which has a predetermined resistance to diffusion of the measurement gas therethrough. Thus, the inner pumping cell 34 communicates with the atmosphere which has diffused in the internal space 36. A pumping voltage from an external power source 40 is applied between the two pumping electrodes 32, 34 of the pumping cell, so that the atmosphere within the internal space 36 is varied by an pumping action of the pumping cell. As is well known in the art, the measurement of the measurement gas is made based on the pumping current which is determined according to the known principle of polarographic analysis.

In this electrochemical element 2, the inner electrically insulating layer 16 is formed on the surface of the solid electrolyte body 4 of the electrochemical pumping cell remote from the outer pumping electrode 32. The solid electrolyte layer 18 is formed on the inner insulating layer 16, and the protective electrode 20 is formed on the outer surface of the solid electrolyte layer 18. Thus, the electrochemical pumping cell, and the layers 16, 18 and 20 are superposed on each other to form an integral laminar structure. The solid electrolyte layer 18 incorporates the outer electrically insulating layer 22, in which the heater 24 is embedded, such that at least the heat-generating portion of the heater 24 is embedded in the highly dense or gas-tight structure of the solid electrolyte layer 18. The protective electrode 20 is electrically connected to the positive electrode 32 of the electrochemical pumping cell, and to the negative terminal of the power source 28 for the heater 24 (more precisely, to the negative lead of the heater 24). Further, the protective electrode 20 is exposed to the atmosphere (measurement gas) to which the outer pumping electrode 32 of the pumping cell is also exposed.

In the instant electrochemical element 2, the inner insulating layer 16 effectively prevents the leak current from the heater 24 from flowing into the electrochemical pumping cell, while the solid electrolyte layer 18 effectively leads the leak current to the protective electrode 20, whereby the adverse effect of the heater leak current is suitably avoided. Furthermore, the protective electrode 20 provided on the outer surface of the solid electrolyte layer 18, i.e., on the outer surface of the element 2, effectively eliminates otherwise possible reduction in the strength of the element 2 and increase in the cost of manufacture.

In addition, the dense structure of the solid electrolyte layer 18 of the instant electrochemical element 2 surrounds at least the heat-generating portion of the heater 24, whereby the heated heat-generating portion embedded in the dense layer 18 is protected from diffusion of its metallic material, or deterioration due to exposure to the measurement gas. Thus, the instant arrangement is advantageous from the standpoint of durability of the heater 24.

Figure 4:
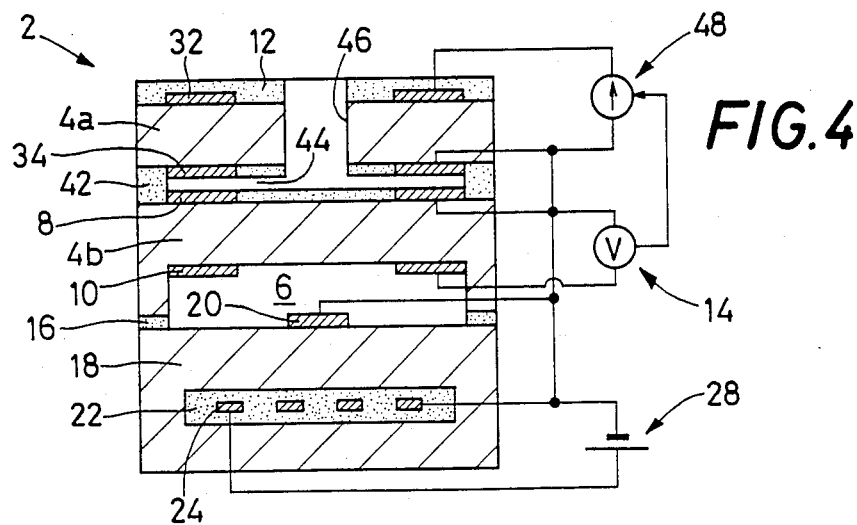
Figure 5:
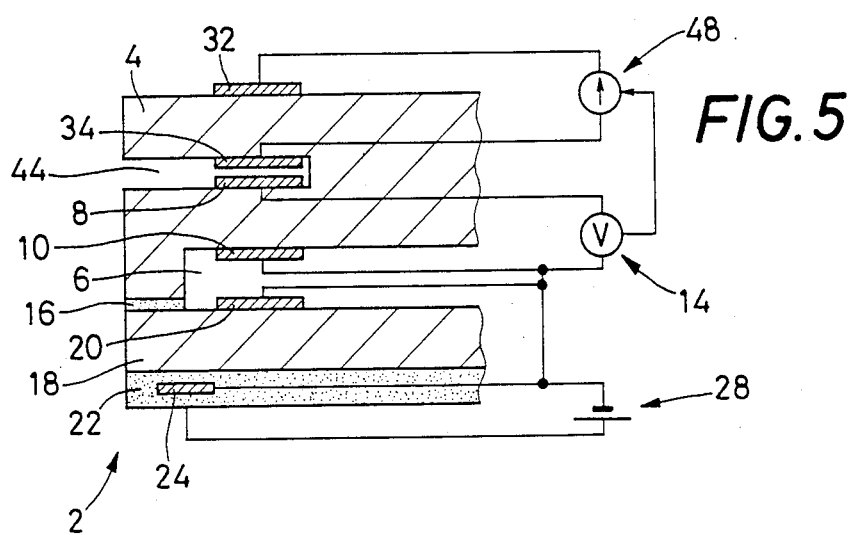
FIG. 5 is a schematic elevational view of a detecting portion provided at one longitudinal end of an electrochemical device according to another embodiment of the invention.

Referring further to FIGS. 4 and 5, there are shown electrochemical elements 2, which are different from the elements 2 of the preceding embodiments. That is, each of the electrochemical elements 2 of FIGS. 4 and 5 is characterized by the use of two electrochemical cells, namely, an electrochemical pumping cell and an electrochemical sensing cell.

In the electrochemical element 2 of FIG. 4, for instance, the electrochemical pumping cell is constituted by a solid electrolyte body 4a, and an outer and inner pumping electrode 32, 34 formed on the opposite major surfaces of the solid electrolyte body 4a, while the electrochemical sensing cell is constituted by a solid electrolyte body 4b, and a measuring and reference electrode 8, 10 formed on the opposite major surfaces of the solid electrolyte body 4b. These two electrochemical cells are electrically insulated from each other by an electrically insulating layer 42 made of alumina or similar material. Between the two cells, there is formed a thin flat space 44 which serves as diffusion-resistance means having a predetermined diffusion resistance. A gas inlet aperture 46 is formed in communication with a central portion of the thin flat space 44, so that the measurement gas in the external measurement-gas space is introduced through the aperture 46 into the thin flat space 44. The introduced measurement gas diffuses through the thin flat space 44 under the predetermined diffusion resistance, so that the measurement gas contacts the inner pumping electrode 34 and the measuring electrode 8 which are disposed in facing relationship with each other, at an outer portion of the space 44.

In the electrochemical element 2 shown in FIG. 5, the thin flat space 44 having the predetermined diffusion resistance is formed in the solid electrolyte body 4 such that the space 44 is directly open to the external measurement-gas space. The electrochemical pumping cell is constituted by a portion of the solid electrolyte body 4 that defines one of opposite inner surfaces of the flat space 44, and the outer and inner pumping electrodes 32, 34 formed in contact with that portion of the body 4. The electrochemical sensing cell is constituted by another portion of the solid electrolyte body 4 that defines the other inner surface of the flat space 44, and the measuring and reference electrodes 8, 10 formed in contact with the above-indicated another portion of the body 4. The measurement gas which has diffused into the thin flat space 44 under the predetermined diffusion resistance contacts the inner pumping electrode 34 of the pumping cell and the measuring electrode 8 of the sensing cell, which are disposed at a relatively inner portion of the flat space 44.

Where the present electrochemical elements 2 of FIGS. 4 and 5 having the electrochemical pumping and sensing cells arranged as described above are used as an oxygen sensor, an electromotive force is induced between the measuring and reference electrodes 8, 10 of the oxygen concentration sensing cell, according to the principle of an oxygen concentration cell, based on a difference in oxygen concentration between the measurement gas which has diffused into the flat space 44 under the predetermined diffusion resistance, and the reference gas (ambient air) existing in the air passage 6. Depending upon the electromotive force thus induced, a pumping current from an external power source 48 is applied between the outer and inner pumping electrodes 32, 34 of the pumping cell, so that an oxygen pumping action is performed so as to control the atmosphere in the flat space 44, adjacent to the inner pumping electrode 34, that is, so that the atmosphere adjacent to the measuring electrode 8 of the oxygen concentration sensing cell is controlled to be a predetermined atmosphere. The oxygen concentration of the measurement gas is determined by detecting a pumping current which flows betwen the two pumping electrodes 32, 34.

In these electrochemical elements 2 of FIGS. 4 and 5, the leak current from the heater 24 is insulated in the same manner as described with respect to the preceding embodiments.

Described more specifically referring to FIG. 4, the inner electrically insulating layer 16 is interposed between the solid electrolyte layer 18 and the solid electrolyte body 4b of the electrochemical sensing cell, such that the layer 16 partially defines the air passage 6. The protective electrode 20 is disposed on the surface of the solid electrolyte layer 18 which is exposed to the air passage 6. The outer electrically insulating layer 22 incorporating the heater 24 is embedded in the solid electrolyte layer 18. The protective electrode 20 is electrically connected to the inner pumping electrode 34 of the pumping cell, the measuring electrode 8 of the sensing cell, and the negative terminal of the power source 28 for the heater 24.

In the example of FIG. 5, the inner insulating layer 16, the solid electrolyte layer 18, and the outer insulating layer 22 having the heater 24 embedded therein are superposed on each other to form an integral laminar structure, as in the element 2 of FIG. 2. The protective electrode 20 is disposed on the surface of the solid electrolyte layer 18 which is exposed to the air passage 6. The electrode 20 is electrically connected to the reference electrode 10 of the electrochemical sensing cell and the negative terminal of the power source 28 for the heater 24.

Therefore, the electrochemical elements 2 shown in FIGS. 4 and 5 also have the same advantages as offered on the preceding examples, namely, reduced output error or improved detecting accuracy, elimination of reduced structural strength and increased production cost, avoidance of output inconsistency due to an electromotive force induced between the protective electrode and the sensing cell electrode based on an oxygen concentration difference therebetween, and prevention of deterioration of the solid electrolyte body by the heater leak current.

The advantages of the electrochemical elements according to the present invention as illustrated above over the known element will be described by reference to FIGS. 6(a), 6(b) and 6(c), which show simplified circuits which are equivalent to the known and present elements.

Figure 6A:
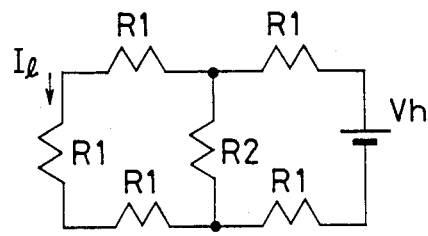
FIGS. 6(a), 6(b) and 6(c) are diagrams showing simplified circuits which are equivalent to known devices and the device according to the present invention.

The equivalent circuit shown in FIG. 6(a) is equivalent to a known electrochemical element wherein a protective electrode is embedded in a solid electrolyte layer, as disclosed in FIG. 3 of Japanese unexamined Patent Application Laid-open Publication No. 59-197851. The equivalent circuit shown in FIG. 6(b) is equivalent to another type of known electrochemical element wherein a protective electrode is disposed in contact with a solid electrolyte of an electrochemical sensing cell, while a heater is disposed on an electrically insulating layer formed on the solid electrolyte of the cell., as disclosed in FIG. 2 of Japanese Patent Application Laid-open Publication No. 57-196148 (corresponding to U.S. Pat. No. 4,400,260), and in FIG. 4 of the Publication No. 59-197851 identified above. Further, the equivalent circuit shown in FIG. 6(c) is equivalent to the electrochemical elements of the electrochemical device of the present invention as illustrated above.

Figure 6B:
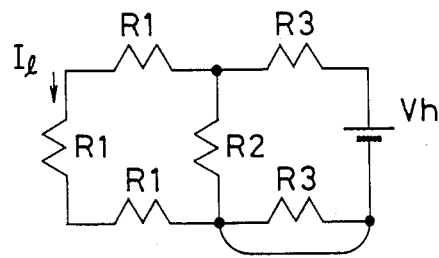
Figure 6C:
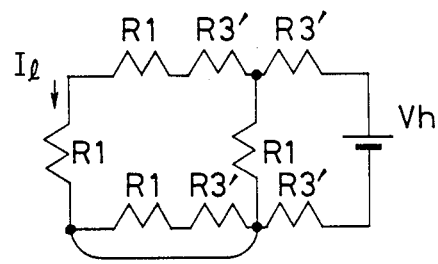

In each of the equivalent circuits of FIGS. 6(a), 6(b) and 6(c), a value $I1$ of the heater leak current flowing to the electrochemical cell is calculated, on the assumption where, $Vh$ (power source voltage for the heater) = 12 V,
$R1$ (resistance of the solid electrolyte) = 100Ω,
$R2$ (resistance of the protective electrode) = 5Ω,
$R3$ (resistance of the insulating ceramic layer) = 200 KΩ,
$R3'$ (resistance of the insulating ceramic layer) = $R3/2$ = 100 KΩ.

The calculated values $I1$ of the heater leak current are 960 μA in the circuit of FIG. 6(a), 0.98 μA in the circuit of FIG. 6(b), and 0.06 μA in the circuit of FIG. 6(c). It follows from the above that the leak current values in the equivalent circuits of FIGS. 6(b) and 6(c) are both well within a practically permissible range of tolerances.

However, the known electrochemical element represented by the equivalent circuit of FIG. 6(a) suffers from an excessively large amount of the heater leak current. This means that the known arrangement of FIG. 6(a) cannot expect the protective electrode alone to provide a sufficient insulating effect. Although the heater leak current $I1$ in the known electrochemical element represented by the circuit of FIG. 6(b) is sufficiently reduced, it is necessary to electrically insulate the protective electrode (i.e., power supply circuit for the heater) and a measuring circuit of the electrochemical cell, relative to each other. This electrical insulation is technically difficult. In the absence of the electrical insulation, there may arise a loop current due to an electromotive force which would be induced between the protective electrode and one of the electrodes of the electrochemical cell. If the electromotive force is 0.5 V while the resistance ($R1$) of the solid electrolyte is 100 Ω, for example, tee loop current amounts to 5 mA, which results in reducing the detecting accuracy of the electrochemical element.

In the electrochemical element of FIG. 6(c) according to the present invention, however, the heater leak current is reduced to a sufficiently low level, while at the same time the loop current is held sufficiently low. If the resistance $R3'$ of the insulating ceramic layer is 100K and the electromotive force is 0.5 V, for example, the loop current is as low as 5 μA.

In the illustrated embodiments in the form of an oxygen sensor, the solid electrolyte bodies (4, 4a, 4b), and the solid electrolyte layer (18) adjacent to the heater 24 are preferably formed principally of an oxygen-ion conductive solid electrolyte material such as zirconia ceramic. However, the solid electrolyte bodies and layer may be formed of other oxygen-ion conductive solid electrolyte materials such as $SrCeO_3$, or a solid solution of $Bi_2O_3$ and rare earth oxides. Further, where the electrochemical element is adapted to determine the concentration of a component other than oxygen, it is obvious that other solid electrolyte materials are selected depending upon the component to be measured.

It is generally desirable that a ceramic material whose major component is alumina or spinel is used for the first and second electrically insulating ceramic layers (22, 16), and the electrically insulating layer (42), which are provided to insulate the current applied to the heater (24) and the leak current from the heater. However, the major component of these insulating layers may consist of other ceramic materials such as borosilicate glass, mullite, steatite, forsterite, cordierite, and zircon.

The protective electrode (20) is preferably formed of a material whose major component consists of a metal selected from the platinum group which includes platinum, palladium, rhodium, iridium, ruthenium and osmium, like the measuring electrode (8), reference electrode (10), outer pumping electrode (32), inner pumping electrode (34), and heater (24). For increased adhesive strength of these electrodes relative to the solid electrolyte body or layer with which the electrodes are co-fired, it is recommended that the powdered metal for the electrodes be mixed with a finely divided powder of a suitable ceramic material such as zirconia or alumina.

While the present invention has been described in its presently preferred embodiments, it is to be understood that the invention is not limited to the details of the illustrated embodiment, and that the invention may be embodied with various changes, modifications and improvements, which may occur to those skilled in the art, without departing from the scope of the invention defined in the appended claims.

For example, while the illustrated electrochemical elements have a single heating portion (heater) on one side of the electrochemical cell (or on one side of the laminar structure of the two electrochemical cells), it is possible that two or more heating portions are provided on the opposite sides of the electrochemical cell or the laminar structure of the two cells, or between the two cells.

It will be understood that other changes and modifications may be made in the construction of the illustrated electrochemical element of the oxygen sensor. Further, the principle of the present invention may apply to a sensor, detector or controller adapted to determine the concentration of components of a fluid other than oxygen, such as nitrogen, carbon dioxide or hydrogen, which involve an electrode reaction.

What is claimed is:

1. An electrochemical device including an electrochemical element having an integrally formed laminar structure comprising:
   at least one electrochemical cell including a first solid electrolyte, and at least one pair of electrodes formed in contact with said first solid electrolyte;
   at least one heating portion including a second solid electrolyte, a first electrically insulating ceramic layer formed in contact with said second solid electrolyte, and a heater electrically insulated from said second solid electrolyte by said first electrically insulating ceramic layer;
   a second electrically insulating ceramic layer interposed between said first solid electrolyte of said at least one electrochemical cell and said second solid electrolyte of said at least one heating portion, so as to electrically insulate said first and second solid electrolytes from each other; and
   a protective electrode formed in contact with sad second solid electrolyte of said at least one heating portion, and electrically connected to at least one of said at least one pair of electrodes of said at least one electrochemical cell.

2. An electrochemical device according to claim 1, wherein said protective electrode is electrically connected to a negative voltage terminal of said heater.

3. An electrochemical device according to claim 1, wherein at least a portion of said protective electrode is substantially exposed to a predetermined gaseous fluid.

4. An electrochemical device according to claim 1, wherein said protective electrode and said at least one of said at least one pair of electrodes of said at least one electrochemical cell are exposed to substantially a same gaseous fluid.

5. An electrochemical device according to claim 1, wherein said second solid electrolyte has a substantially gas-tight structure which surrounds at least a heat-generating portion of said heater.

6. An electrochemical device according to claim 1, wherein said at least one electrochemical cell includes an electrochemical pumping cell having a pair of pumping electrodes, and an electrochemical sensing cell having a measuring electrode and a reference electrode, and wherein said protective electrode is electrically connected to one of said pair of pumping electrodes of said pumping cell and said measuring electrode of said sensing cell, said one pumping electrode and said measuring electrode being exposed to substantially a same gaseous fluid.

7. An electrochemical device according to claim 1, wherein said at least one electrochemical cell includes an electrochemical pumping cell, and an electrochemical sensing cell having a reference electrode, and wherein said protective electrode is electrically connected to said reference electrode of said sensing cell.

* * * * *